United States Patent [19]

Ackerman et al.

[11] Patent Number: 4,774,946
[45] Date of Patent: Oct. 4, 1988

[54] NASAL AND ENDOTRACHEAL TUBE APPARATUS

[75] Inventors: Bernard Ackerman, Metuchen, N.J.; Robert Landis, New York, N.Y.

[73] Assignee: Ackrad Laboratories, Inc., Cranford, N.J.

[21] Appl. No.: 930,966

[22] Filed: Nov. 12, 1986

Related U.S. Application Data

[63] Continuation of Ser. No. 555,705, Nov. 28, 1983, abandoned.

[51] Int. Cl.⁴ .................. A61M 15/08; A62B 7/00
[52] U.S. Cl. ..................... 128/207.18; 104/179; 128/DIG. 26
[58] Field of Search ............... 128/DIG. 26, 207.14, 128/207.15, 267.17, 207.18, 200.26, 203.18, 206.27, 267.11, 267.11, 727, 201.23, 267.13, DIG. 15, 97, 163, 157; 604/179, 174, 180; 2/205, 422, 173, 171.2, 171.8, 183, 206, 209.1, 416–419, DIG. 11; 24/30

[56] References Cited

U.S. PATENT DOCUMENTS

| | | | |
|---|---|---|---|
| 2,292,568 | 8/1942 | Kanter et al. | 128/204.11 |
| 2,693,800 | 11/1954 | Caldwell | 128/207.18 |
| 3,156,923 | 11/1964 | Timm | 2/419 |
| 3,209,755 | 10/1965 | McCarthy et al. | 604/174 |
| 3,288,137 | 11/1966 | Lund | 128/DIG. 26 |
| 3,576,364 | 4/1971 | Gillement | 248/205.2 |
| 3,730,179 | 5/1973 | Williams | 128/207.18 |
| 3,955,570 | 5/1976 | Hutler | 128/201.23 |
| 4,025,015 | 5/1977 | Kolic | 128/DIG. 26 |
| 4,055,173 | 10/1977 | Knab | 128/201.23 |
| 4,191,180 | 3/1980 | Colley et al. | 128/DIG. 26 |
| 4,313,437 | 2/1982 | Martin | 128/207.17 |
| 4,367,735 | 1/1983 | Dali | 128/207.18 |
| 4,480,639 | 11/1984 | Peterson et al. | 128/DIG. 26 |

FOREIGN PATENT DOCUMENTS

| | | | |
|---|---|---|---|
| 2390116 | 1/1979 | France | 2/DIG. 11 |
| 32355 | 10/1964 | German Democratic Rep. | 2/419 |
| 153193 | 12/1981 | German Democratic Rep. | 128/207.18 |
| 1350750 | 4/1974 | United Kingdom | 128/200.27 |
| 8203548 | 10/1982 | World Int. Prop. O. | 128/207.13 |

*Primary Examiner*—Edward M. Coven
*Assistant Examiner*—K. M. Reichle
*Attorney, Agent, or Firm*—Lackenbach Siegel Marzullo & Aronson

[57] ABSTRACT

This invention relates generally to tube apparatuses and more particularly to tube apparatuses that are connected to a source of pressurized air that forces air into the lungs of a recipient. The invention comprises an elongated flexible tube connected to a pair of nasal tubes positioned in the nares of the nose of the recipient. The ends of the elongated tube are connected to an air pressure control device. The nasal tubes include bulbous portions that seat and seal the nasal tubes in the nares. The invention also includes a yoke that adjustably connects the elongated tube to a headband on the head of the recipient. An alternate embodiment uses an endotracheal tube apparatus that is connected to the source of pressurized air for forcing pressurized air into the lungs of the recipient.

1 Claim, 2 Drawing Sheets

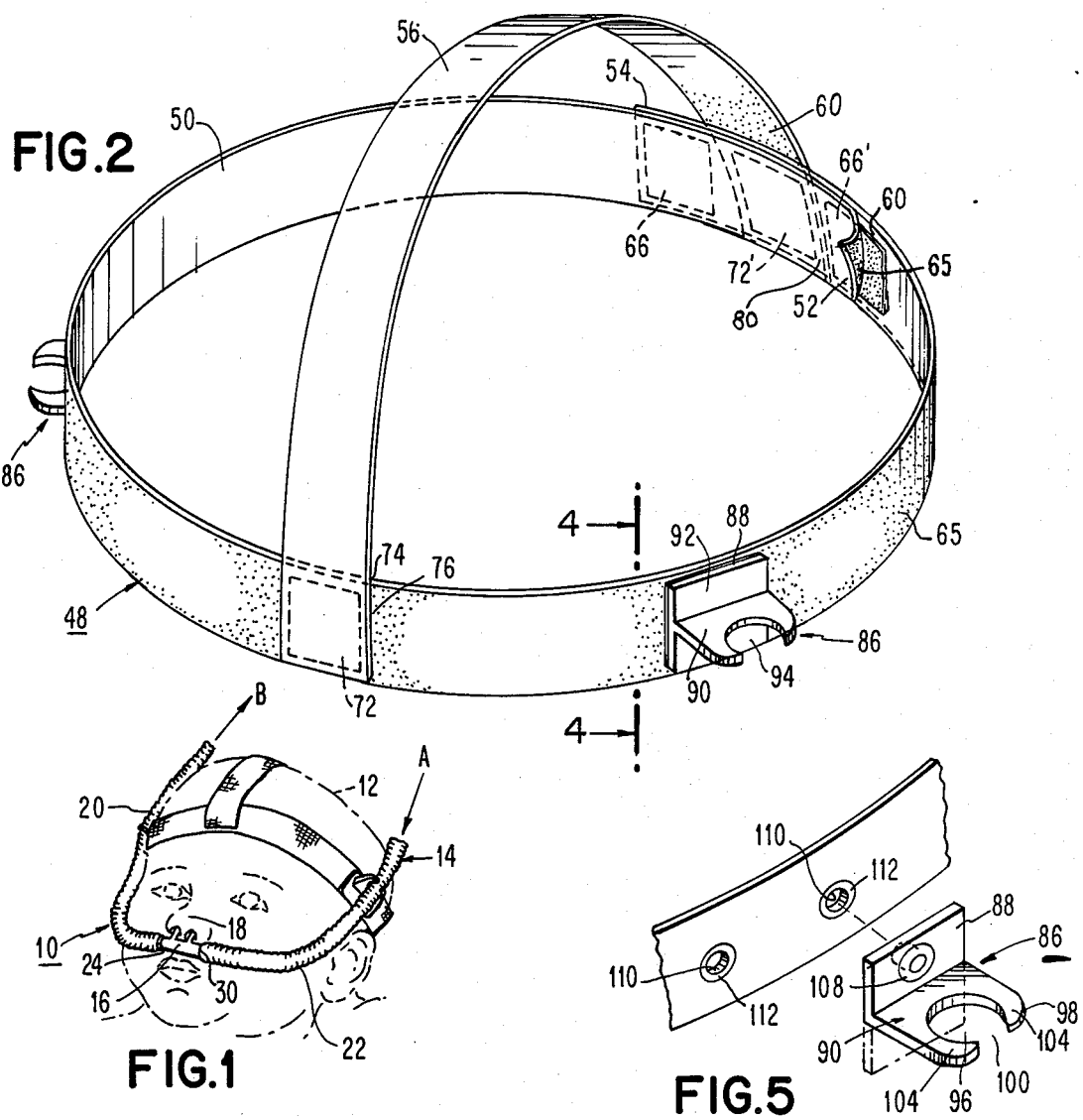
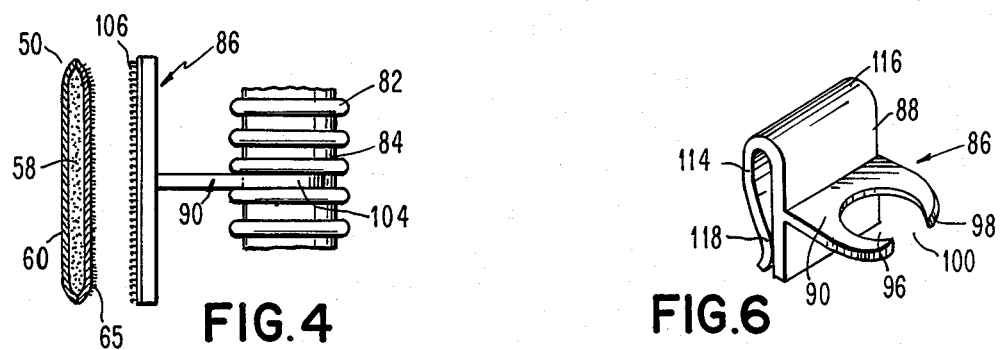
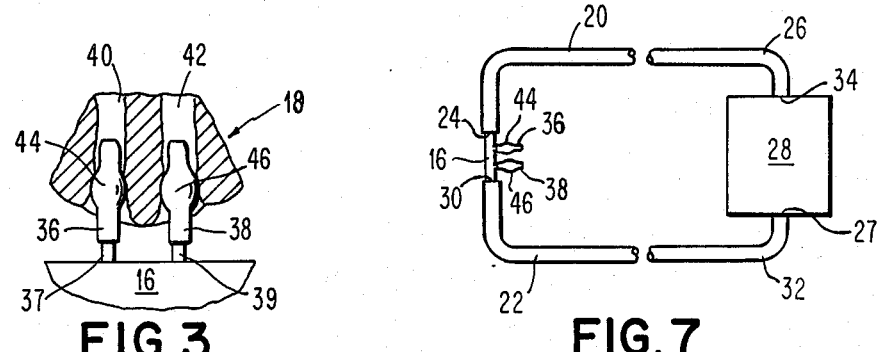

4,774,946

NASAL AND ENDOTRACHEAL TUBE APPARATUS

This application is a continuation of application Ser. No. 555,705, filed 11/28/83, now abandoned.

This invention relates generally to nasal cannulae and endotracheal tube apparatus that are connected to a source of pressurized air that forces pressurized air into the lungs of a patient or recipient.

One particular area of use of nasal cannulae is for a recently born infant in need of a lung exercise program. A pair of nasal cannulae attached to a pair of elongated tubes are inserted into the nares or nostrils of the infant. The other ends of the elongated tubes are connected to a continuous positive airway pressure (CPAP) machine, which introduces oxygen-enriched air at a pressure slightly above atmospheric pressure through the apparatus into the infant's lungs. The infant, after absorbing the oxygen content of the pressurized air, is forced to expel the carbon dioxide from its lungs against the positive pressure of the CPAP machine. This system of pressurized-air lung exercise is usually mounted to the infant for about two or three days for twenty-four hours a day. The apparatus forces the infant to exercise respiratorily by overcoming the positive pressure from the CPAP machine.

OBJECTS OF THE INVENTION

Accordingly, it is an object of this invention to provide a nasal cannulae apparatus that can be firmly and adjustably secured to a recipient.

It is another object of this invention to provide a nasal cannulae apparatus which provides a secure and sealed positioning of the nasal cannulae that are inserted in the nares of the recipient.

It is a further object of this invention to provide a pair of nasal cannulae connected to a CPAP machine that securely sets into the recipients nares in a way that seals off the nose from leakage of pressurized air either going into the nose to the lungs or returning from the lungs and from the nose.

It is still another object of this invention to provide a nasal cannulae apparatus that sealably seats the nasal cannulae in the nares so that the nasal cannulae are inhibited from moving or sliding out therefrom.

It is yet a further object of this invention to provide a nasal cannulae apparatus that can be selectively adjusted into place with a headband mounted to the head of the recipient.

It is yet another object of this invention to provide a nasal cannulae apparatus that connects a pair of nasal cannulae with elongated tubes to a CPAP machine which provides a means for selectively adjusting the length of the tubes to a headband in a light holding tension.

It is yet a further object of this invention to provide an endotracheal tube apparatus that provides a secure and sealed positioning between the elongated tubes from a CPAP machine and the lungs of the recipient.

SUMMARY OF THE INVENTION

The nasal apparatus in accordance with the present invention comprises an elongated flexible tube having a middle connecting portion positioned proximately below the nose of the recipient and having first and second flexible tube portions each connected at an end to the connecting portion and at the other end to a CPAP unit that provides slightly pressurized air to the apparatus. Each first and second nasal cannula is provided with a globular, First and second nasal cannulae are insertedly positioned in the right and left nares of the infant, or recipient, and are connected to the middle portion of the elongated tube towards the first and second tube portions, respectively. Each first and second nasal cannula is provided with a globular, or bulbous, portion that is inserted into and seated within each nare firmly against the walls of each nare so as to provide a sealed airway to the recipient's lungs. A soft, cotton flannel headband mounted to the head of the patient includes a first band positioned across the forehead, around the sides of the head, and across the back of the head. The first band was overlapping portions at the back of the head provided with hook-and-loop fastening means, preferably of the Velcro type to adjustably connect the first headband to itself around the head. A second band passes over the top of the head and is adjustably connected at the forehead area and the rear of the head to the first band by similar hook-and-loop fastening means. The first and second tube portions are corrugated and have alternate circular ridges and grooves. In one embodiment of the invention, a pair of yokes each having a flat member having a transversely extending shelf forming a circular hole of about the same diameter as the diameter of the circular groove and having an opening between two prongs leading to the hole can be selectively connected to any of the circular grooves of the first and second tube portions. The opposite side of each flat member also has a like, hook-and-loop fastener that can be connected to the headband.

An alternate embodiment comprises an endotracheal tube that is positioned in the trachea of the patient and having one end extending from the mouth of the patient. An adapter connects the endotracheal tube with the middle connecting portion of the first and second tube portions leading to the CPAP machine.

The present invention will be better understood and the main objects and important features will become apparent from the following detailed description which, in conjunction with the annexed drawings, discloses and illustrates the preferred embodiments or modifications of the present invention and what is believed to be the best mode of practice according to the principles thereof.

BRIEF DESCRIPTION OF THE DRAWINGS

FIG. 1 is a perspective view of the nasal apparatus according to the present invention as mounted to the head of an infant;

FIG. 2 is a perspective view of the headband;

FIG. 3 is a sectional view of the mounted nasal apparatus schematically showing the positioning of nasal cannulae inserted in the nares of an infant;

FIG. 4 is a section view of a mounting yoke taken through line 4—4 of FIG. 2;

FIG. 5 is an alternate embodiment of a mounting yoke shown in perspective;

FIG. 6 is another alternate embodiment of a mounting yoke shown in perspective;

FIG. 7 is a schematic view of the apparatus that includes the CPAP machine;

DESCRIPTION OF THE PREFERRED EMBODIMENTS

Figure 8:
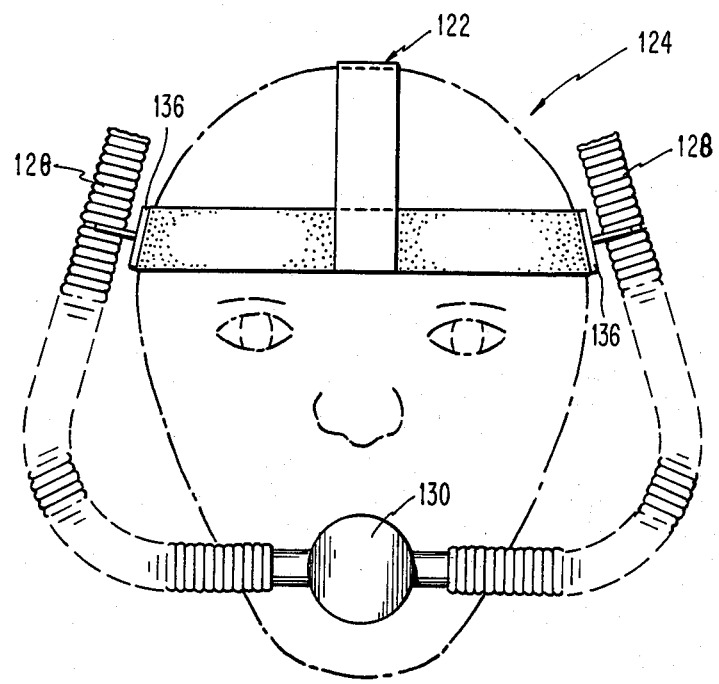
FIG. 8 is a front view of an endotracheal tube apparatus connected to the head of an infant according to the present invention.

Reference is now made specifically to the drawings in which identical or similar parts are designated by the same reference numerals throughout.

A nasal cannulae apparatus 10 is shown in FIG. 1 in a perspective view mounted with a recipient, preferably an infant 12. Apparatus 10 includes an elongated hollow tube 14 having a rigid hollow middle connecting portion 16 positioned proximately below the nose 18 of infant 12 and first and second flexible tube portions 20 and 22, respectively. First flexible tube portion 20 has opposed ends 24 and 26, with one end 24 attached to connecting portion 16 on the right side of the nose 18 and the other end 26 attached to one side 34 of the continuous positive airway pressure, or CPAP unit 28, which is shown in FIG. 7.

The second flexible tube portion 22 has opposed ends 30 and 32, with one end 30 attached to connecting portion 16 on the left side of nose 18 and the other end 32 attached to the other side 27 of the CPAP unit 28.

As shown in FIG. 3, first and second nasal cannulae 36 and 38 are positioned in the right and left nares 40 and 42, respectively, of the nose 18.

First nasal cannula 36 is connected to middle connecting portion 16 proximate to end 24 of first tube portion 20 via a rigid connector tube 37, extending perpendicularly upward from connector 16, and second nasal cannula 38 is connected to middle connecting portion 16 proximate to end 30 of second tube portion 22 via a rigid connector tube 39 also extending perpendicularly upward from connector 16. First and second nasal cannulae 36 and 38 have first and second globular, or bulbous, portions 44 and 46, respectively, which are seated against the inner walls of the first and second nares 40 and 42, respectively. Bulbous portions 44 and 46 are seated within the nares so as to seatingly and sealingly engage first andd second nasal cannulae 36 and 38 in the nares of the nose. This results both in the firm positioning of the bulbous portions in the nares and in aiding in maintaining a set, desirable working pressure in the apparatus. Nasal cannulae 36 and 38 are made of a soft, flexible plastic material.

First and second bulbous portions 44 and 46 also act to seat nasal cannulae 36 and 38 in the nares of the nose, since the bulbous portions are preferably slightly larger than the openings to the nares, which will spread slightly upon entry of the bulbous portions. Bulbous portions 44 and 46 act not only to seal off the nares between the walls of the nose and outside surfaces of nasal cannulae 36 and 38 as explained above, but also to tend to inhibit the nasal cannulae from sliding out of the nares. Thus, both a sealing action and a securing action result.

FIG. 2 shows a headband 48 that includes a first band 50 that extends around the infant recipient substantially across the forehead, above the ears, and the rear of the head. First band 50 has a pair of free end portions 52 and 54 that have connecting mutually underlapping and overlapping surfaces 65 and 60, respectively, preferably at the rear of the head of the recipient. A second band 56 is removably connected to first band 50 at the forehead and at the back of the head. Second band 56 passes over the midtop of the head between the forehead and the back of the head.

First and second bands 50 and 56 each are made of an elongated, substantially flat, elastic foam material forming an inner foam strip 58 and two soft inner and outer covers, 60 and 65 surrounding each strip 58. Inner cover 60 of first and second bands 50 and 56 is made of a soft absorbent material, such as cotton flannel. Outer cover 65 is the loop portion of a hook-and-loop fastener capable of mating with the hook portion of the hook-and-loop fastener.

A first pair of substantially flat gripping tabs 66 and 66' each having a hook portion of the hook-and-loop fastener adjustably and removably connect band 50 to itself at the back of the head. Gripping tab members 66 and 66' are positioned on free end portion 54 with a 1 to 2-inch space between them. Gripping tab members 66 and 66' are generally square. One side of each gripping member has an adhesive material (not shown) for attachment to the surface 60; the opposite side has a hook portion of a hook-and-loop fastener material, such as Velcro. The hooks of gripping members 66 and 66' removably grip the loops of outer cover 65 in two places opposite to the gripping members 66 and 66'. Gripping members 66 and 66' enable band 50 to be selectively tightened or loosened around the infant's head.

Likewise, a second pair of substantially flat gripping tab members 72 and 72' each having loops adjustably and removably connect a second band 56 to first band 50. Second band 56 overlaps first band 50 at the forehead and the back of the head at connecting front and rear mutually overlapping and underlapping surfaces 74 and 76 at the forehead and similarly at the back of the head. The second pair of gripping members 72 and 72' are positioned at the particular overlapping and underlapping surfaces. The second pair of gripping members 72 and 72' are similar to first pair of gripping members 66 and 66' and are also flat and square. One side of each gripping member 72 and 72' has adhesive material connected to the overlapping surfaces 76 and 80 and the opposite side has hooks which adheres to the loops of underlapping surfaces 74 and 65. Thus, second band 56 is adjustably and removably connected to first band 50, and second band 56 can be selectively tightened or loosened over the infant's head.

First and second flexible tube portions 20 and 22 are corrugated so as to form a plurality of alternating circular ridges 82 and circular grooves 84. Circular ridges 82 have ridge outer diameters and circular grooves 84 have groove outer diameters, the ridge outer diameter being greater than the groove outer diameter.

As shown in FIGS. 2 and 4, a pair of yokes 86 adjustably connect first and second tube portions 20 and 22 to headband 48, specifically to first band 50. Yokes 86 cooperate with headband 48 to selectively and firmly position flexible tube 14 with the head of the infant. Each of the pair of yokes 86 includes a substantially flat, square mounting member 88 having opposed walls and a shelf 90 extending transversely, or substantially perpendicularly, from one wall. Shelf 90 is preferably laterally positioned midway between opposed edge 92 and the other opposed edge 94, as shown in FIG. 2. Shelf 90 forms a circular hole 96 at the outer edge 98 of shelf 90. Circular hole 96 has an opening 100 defined by a pair of opposed prongs 104 spaced apart a predetermined distance. The hole diameter is substantially equal to the groove outer diameter and the distance between prongs 104 is less than the groove outer diameter. The surface of mounting member 88 opposite the surface on which the shelf 90 is positioned has the hook portion of hook-and-loop fastener 106 connected to it. Thus, each yoke 86 is selectively and removably attached to first band 50 by way of the hook portion 106 of hook-and-loop fastener adhering to the first band 50 at selected positions at each side of the infant as shown in FIG. 1. With the yokes 86 in place, the tube portions 20,22 can be removably attached thereto at any selected circular grooves 84 in the first and second tube portions 20 and 22. This is accomplished by squeezing a circular groove 84 into hole 96, where the particular circular groove 84 of the particular tube portion 20 or 22 flexibly moves to a compressed state when it is passed through opening 100 into circular hole 96, and where it then resiliently returns to its normal state. Elongated tube portions 20 and 22 are preferably made of a flexible, resilient, plastic material. In this manner, after the first and second nasal tubes 36 and 38 are inserted into nares 40 and 42, the length of first and second tube portions 20 and 22 between the first and second nasal tubes 36 and 38 in the nose and headband 48 can be adjusted to provide a light holding tension between the headband and the nasal tubes.

Alternate embodiments of yokes 86 are shown in perspective in FIGS. 5 and 6. In FIG. 5, yoke 86 is provided with a suitable snap-like fastener, such as snap-in dowel 108 that extends outwardly from the wall of mounting member 88 opposite shelf 90. At least two snap-in holes 110 are provided in the first band 50 at each side of the head of the infant. Snap-in holes 110 are provided with circular metal rungs 112 that are capable of snapping around a circular groove (not shown) formed in dowel 108 or in other known manners known in the art, such as one employing detent means. Each dowel 108 can be selectively mounted to one of the snap-in holes 110 to provide a selective attachment of the apparatus to headband 48. FIG. 6 shows yoke 86 having a clamping wall 114 that is biasedly connected to the top edge 116 of mounting member 88 and that extends lateral and proximate to outside surface of the wall of mounting member 88. Clamping wall 114, which is flexibly and biasedly attached to yoke 86, and in close association with mounting member 88, has a pressing portion 118 which is biased towards the outer surface of mounting member 88 so that each yoke 86 can be selectively positioned at each side of the recipient's head to clamp the cloth of first band 50 between each mounting member 88 and associated clamp wall 114 so that first band 50 is gripped at each pressing portion 118 and the surface of each mounting member 88.

Figure 9:
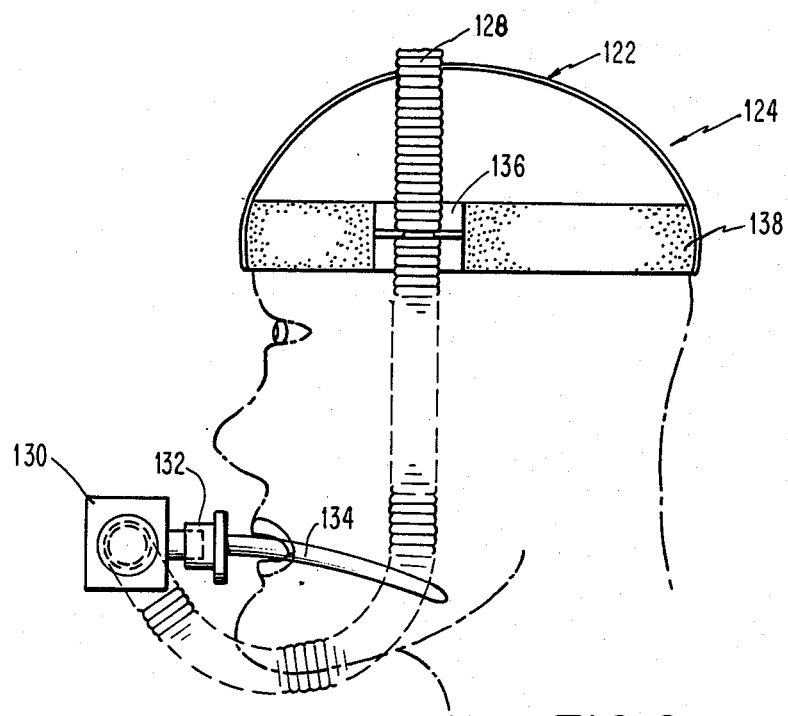
FIG. 9 is a side view of the endotracheal tube apparatus shown in FIG. 8.

An alternate embodiment of apparatus 10 as illustrated in FIGS. 1-7 is shown in FIGS. 8 and 9. A headband 122 similar to headband 48 shown in FIG. 2 is shown mounted to the head of an infant 124. Inlet and outlet tubes 126 and 128 respectively from the CPAP unit (not shown) are connected to a T-connector 130 positioned directly in front of the mouth of the infant. An adapter 132 is connected at one side to a T-connector at one side and to an endotracheal tube 134 at the other side. Endotracheal tube 134 leads down the trachea, or windpipe, of the infant recipient to the lungs. The construction and arrangement of endotracheal tube 134 is known in the art and will not be discussed in detail here. It is sufficient to say that endotracheal tube 134 forms a ventilation passage for passing pressurized air to the lungs of the recipient via inlet tube 126 and for passing the carbon dioxide expelled by the recipient over the pressure of the incoming pressurized air in the endotracheal tube to outlet tube 128.

As seen in FIGS. 8 and 9, inlet and outlet tubes 126 and 128 are supported at yokes 136, which are analogous to yokes 86 discussed previously. Yokes 136 are supported by first band 138, which is analogous to first band 50 discussed previously.

Although the present invention has been described in some detail by way of illustration and example for purposes of clarity of understanding, it will, of course, be understood that various changes and modifications may be made in the form, details, and arrangements of the parts without departing from the scope of the invention as set forth in the following claims.

What is claimed is:

1. A nasal cannulae apparatus adapted to be connected to a continuous positive airway pressure unit and to the nose of an infant, the continuous positive airway pressure unit sending oxygen enriched air to the lungs of the infant and receiving carbon dioxide from the lungs of the infant, comprising, in combination, an elongated tube having a rigid, hollow middle connecting portion adapted for positioning proximately below the nose of the infant, said elongated tube including first and second flexible tube portions each having opposed ends, one of said ends of each tube portion being fluidically secured to said middle connecting portion and the other of said ends being adapted for connection to the continuous positive pressure airway unit, first and second flexible nasal cannulae adapted to be insertedly positioned in the first and second nares, respectively, of the infant, said first nasal cannula being positioned at said middle connecting portion proximate to said one end of said first tube portion and said second nasal cannula being positioned at said middle connecting portion proximate to said one end of said second tube portion, said first and second nasal cannula being adapted to pass the oxygen enriched air to the lungs of the infant infant and to receive the carbon dioxide from the lungs of the infant, first and second rigid connector tubes fluidically secured to and extending perpendicularly upward from said middle connecting portion, said first and second connector tubes being fluidically secured to said first and second flexible nasal cannulae, respectively, seating and sealing means associated with said first and second nasal cannulae for sealingly engaging each said first and second nasal cannula in the nares of the infant, headband means adapted to be removably fastened to the head of the infant, said first and second flexible tube portions forming a plurality of alternating circular ridges and circular grooves, said ridges having ridge diameters and said circular grooves having groove diameters, said ridge diameters being greater than said groove diameters, yoke means for selectively and firmly attacking said first and second tube portions to said headband means at a plurality of selected positions to selectively adjust the distance between said seating and sealing means and said headband means, said yoke means including a pair of substantially flat mounting members, each mounting member having a first side surface and a second reverse side surface and a shelf extending transversely from said first side surface, said shelf having an edge opposite and lateral to said mounting member, said shelf defining a circular hole adjacent to said edge, said edge having a pair of spaced, opposed prongs spaced apart at a distance and defining a slot opening to said hole, the diameter of said partially circular hole being substantially equal to said groove diameters and said distance between said prongs being slightly less than said groove diameters, each said mounting member being attached to one of said first and second tube portions by a selected groove being positioned within said circular hole, said first and second flexible tube portions being capable of being squeezed at said groove diameters so as to pass through said slot into said hole, and said yoke means further comprising attaching means connected to each of said second side surfaces removably connecting said mounting member to said headband means.

* * * * *